United States Patent
Montgomery et al.

(10) Patent No.: US 6,387,886 B1
(45) Date of Patent: May 14, 2002

(54) METHOD FOR THE TREATMENT OF SEVERE CHRONIC BRONCHITIS (BRONCHIETASIS) WITH AN AEROSOLIZED ANTIBIOTIC

(75) Inventors: Alan B. Montgomery, Medina; William R. Baker, Bellevue, both of WA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/868,299

(22) PCT Filed: Dec. 17, 1999

(86) PCT No.: PCT/US99/30235

§ 371 Date: Nov. 28, 2001

§ 102(e) Date: Nov. 28, 2001

(87) PCT Pub. No.: WO00/35461

PCT Pub. Date: Jun. 22, 2000

Related U.S. Application Data (60) Provisional application No. 60/112,984, filed on Dec. 17, 1998.

(51) Int. Cl.⁷ ............................................. A61K 31/70
(52) U.S. Cl. ............................ 514/34; 514/37; 514/39; 514/41
(58) Field of Search ............................. 514/34, 37, 39, 514/41

(56) References Cited

U.S. PATENT DOCUMENTS

| | | | | |
|---|---|---|---|---|
| 5,141,674 A | * | 8/1992 | Leigh | 252/305 |
| 5,512,269 A | * | 4/1996 | Vedia et al. | 424/45 |
| 5,522,385 A | * | 6/1996 | Lloyd et al. | 128/203.26 |

* cited by examiner

*Primary Examiner*—Raymond Henley, III
(74) *Attorney, Agent, or Firm*—Dennis K. Shelton; David P. Lentini; Robert P. Blackburn (57) ABSTRACT

The present invention is directed to a method for the treatment of severe chronic bronchitis, i.e., bronchiectasis, using a concentrated aminoglycoside antibiotic formulation delivering the antibiotic to the lung endobronchial space, including alveoli, in an aerosol or dry powder having a mass medium diameter predominately between 1 to 5 microns.

22 Claims, 4 Drawing Sheets

METHOD FOR THE TREATMENT OF SEVERE CHRONIC BRONCHITIS (BRONCHIETASIS) WITH AN AEROSOLIZED ANTIBIOTIC

This application is a 371 of PCT/US99/30234 filed Dec. 17, 1999which claims benefit of U.S. Provisional Application No. 60/112,984 filed Dec. 17, 1998.

FIELD OF THE INVENTION

The invention relates to methods and compositions for the treatment of severe chronic bronchitis or bronchiectasis by endobronchial delivery of aminoglycoside antibiotic compounds, such as tobramycin. In particular, the invention concerns formulations including aminoglycoside powders or concentrated solutions having pH between 5.5 and 7.0. The formulations permit delivery of aminoglycoside antibiotic compounds to the lung endobronchial space of airways in dry powder form or as an aerosol having mass medium average diameter predominantly between 1 to $5\mu$. The formulated and delivered efficacious amount of aminoglycoside antibiotic compound, such as tobramycin, is sufficient for treatment and prophylaxis of acute and chronic endobronchial infections, particularly those caused by the bacterium *Pseudomonas aeruginosa*. In other aspects, the invention relates to the endobronchial delivery of effective amounts of an aminoglycoside antibiotic, such as tobramycin, to patients with bronchiectasis with *P. aeruginosa* to cause substantially complete eradication of the organism. The novel formulations have small volume yet deliver effective doses of aminoglycoside antibiotic compounds to the site of the infection.

BACKGROUND OF THE INVENTION

Bronchiectasis is defined as irreversible abnormal dilatation of the airways. Bronchiectasis can be caused by either acquired or congenital mechanisms that disrupt the normal processes of airway clearance and/or host defense. These causes may include ciliary motility disorders and cystic fibrosis (CF), or processes that cause persistent damage, such as a bacterial or viral pneumonia. Defects in host defense such as agammaglobulinemia, or mechanical processes such as foreign bodies that cause post-obstructive infection can also result in bronchiectasis (Barker, A. F. et al., "Bronchiectasis: update of an orphan disease," *Am Rev Respir Dis*; 137(4):969–78(1988)). Morbidity from bronchiectasis is caused by persistent airway infection. Treatment of infection may reduce morbidity. The microbiology of lung infections in CF has been well characterized, with *Staphylococcus aureus, Haemophilus influenzae,* and *Pseudomonas aeruginosa* colonizing in an age-related sequence. *P. aeruginosa* infects 60% of all patients with CF (Cystic Fibrosis Foundation, *Cystic Fibrosis Foundation Patient Registry, Annual Data Report* 1992, (1993)). However, the microbiology of bronchiectasis in patients without CF has not been well-characterized. One retrospective study of bronchiectasis found the most frequently isolated organisms to be *P. aeruginosa* (30.9% of patients), *Haemophilus influenzae* (30.1%), mycobacteria (22.8%), *Mycobacterium avium-intracelluare* (17.1%), other Gram-negative bacilli (13%), and *Streptococcus pneumoniae* (10.6%) (Nicotra, M. B. et al., "Clinical, pathophysiologic, and microbiologic characterization of bronchiectasis in an aging cohort," *Chest* 108(4):955–61 (1995)).

Clinically, bronchiectasis is characterized by chronic airway infection, associated with intermittent exacerbations. Infection may manifest by expectoration of purulent sputum, fever, malaise, and weight loss. The density of *P. aeruginosa* in sputum in patients with exacerbations of bronchiectasis has been estimated at $10^7$ cfu/mL (Currie D. C. et al., "Simple method of monitoring colonizing microbial load in chronic bronchial sepsis: pilot comparison of reduction in colonizing microbial load with antibiotics given intermittently and continuously," *J Clin Pathol* 40:830–836 (1987)). Exacerbations may be treated with oral or parenteral antibiotics, but the options for treatment of *P. aeruginosa* are limited. One common regimen, a 14–21 day course of parenteral aminoglycoside in combination with a third-generation cephalosporin, is widely used but has several disadvantages. The penetration of parenterally-administered aminoglycosides into bronchial secretions is poor and thus hill doses must be given in order to achieve high sputum concentrations (Pennington J. E., "Penetration of antibiotics into respiratory secretions," *Rev Infect Dis* 3(1):67–73 (1981)). High doses and multiple courses of therapy lead to high serum concentrations and increase the risk of serious adverse effects, such as ototoxicity and nephrotoxicity. Treatment of patients with bronchiectasis with *P. aeruginosa* seldom, if ever, eradicates the organisms—most of the treatment benefit from either oral or IV antibiotics just suppresses growth, with regrowth occurring after discontinuation of antibiotic therapy. Therefore, any method that can eradicate infection for any period of time would be useful, novel and an advance in the art.

Tobramycin is commonly prescribed for the treatment of serious infections with *P. aeruginosa*. It is an aminoglycoside antibiotic produced by the actinomycete, *Streptomyces tenebrarius*. Low concentrations of tobramycin ($<4\ \mu g/mL$) are effective in inhibiting the growth of many Gram-negative bacteria and under certain conditions may be bactericidal (Neu. H. C., "Tobramycin: an overview," *J Infect Dis* 134, Suppl: S3–19 (1976)). Tobramycin is poorly absorbed across mucosal surfaces, necessitating parenteral administration. Tobramycin activity is inhibited by purulent sputum: high concentrations of divalent cations, acidic conditions, increased ionic strength and macromolecules that bind the drug all inhibit tobramycin in this environment. It is estimated that 5–10× higher concentrations of tobramycin are required in the sputum to overcome these inhibitory effects (Ledy J. et al., "Bioactivity of gentamicin in purulent sputum from patients with cystic fibrosis or bronchiectasis: comparison with activity in serum," *J Infect Dis* 148(6):1069–76 (1983)).

Delivery of the poorly absorbed antibiotic tobramycin to the airway by the aerosol route of cystic fibrosis (CF) patients has been documented using the aerosol route. Much of this work has been done toward treatment of chronic lung infections with *P. aeruginosa* in cystic fibrosis (CF) patients. A multicenter, double blind, placebo-controlled, crossover trial of 600 mg tid of aerosolized tobramycin for endobronchial infections due to *P. aeruginosa* in 71 CF patients demonstrated a significant reduction in sputum density of this pathogen as well as improved spirometry in the treatment group. Emergence of *P. aeruginosa* strains highly resistant to tobramycin (defined as MIC >128 $\mu g/mL$) was comparable in the placebo and treatment groups. The presence in the sputum of Gram-negative organisms other than *P. aeruginosa* intrinsically resistant to tobramycin occurred with equal frequency during administration of tobramycin or placebo (Ramsey B. et al., "Response to Letter to the Editor: Aerosolized tobramycin in patients with cystic fibrosis," *N Engl J Med* 329:1660 (1993)).

Although this regimen was found to be both safe and efficacious, it is costly and inconvenient. A survey of the MICs for *P. aeruginosa* isolates from initial sputum cultures for patients at the Children's Hospital CF Center, Seattle, Wash., in 1993 found that 90% of isolates had MICs <16 μg/mL and 98% of all isolates had MICs ≦128 μg/mL. This survey suggested that achieving a sputum tobramycin concentration of 128 μg/mL should treat the endobronchial infection in CF patients (Levy J. et al., "Bioactivity of gentamicin in purulent sputum from patients with cystic fibrosis or bronchiectasis: comparison with activity in serum," *J Infect Dis* 148(6):1069–76 (1983)).

A randomized, cross-over study compared the ability of several nebulizers to deliver tobramycin by measuring peak sputum tobramycin concentrations in samples collected ten minutes after completion of the aerosol dose. This study used a new formulation. TOBI®, PathoGenesis Corporation, Seattle, Wash., containing 60 mg/mL, tobramycin in 5 mL one quarter (¼) normal saline. The Pari® LC jet nebulizer, Pari Respiratory Equipment, Inc., Richmond, Va., delivered a mean peak sputum tobramycin concentration of 678.8 μg/g (s.d. 661.0 μg/g), and a median peak sputum concentration of 433.0 μg/g. Only 13% of patients had sputum levels ≦128 μg/g: 87% of patients achieved sputum levels of ≧128 μg/g (Eisenberg, J. et al., "A Comparison of Peak Sputum Tobramycin Concentration in Patients With Cystic Fibrosis Using Jet and Ultrasonic Nebulizer Systems. Aerosolized Tobramycin Study Group," *Chest* 111 (4):955–962 (1997)). This nebulizer completes nebulization in a short time (ten minutes) and produces particles of an ideal mass median aerodynamic diameter (3.3 μm).

Recently, the Pari® LC jet nebulizer has been slightly modified with the addition of one-way flow valves, and renamed the Pari® LC Plus. In vitro experiments using a test lung suggest that the Pari® LC Plus delivers up to 20% more drug than the Pari® LC jet nebulizer. The particle size is identical. The one-way valves also decrease the potential for accidental spillage and allow for the use of an expiratory filter. For these reasons, the Pari® LC Plus jet nebulizer was selected for use in two large Phase 3 trials of TOBI for chronic *P. aeruginosa* infection in CF patients. Preliminary data from these Phase 3 studies show that mean peak sputum tobramycin concentrations achieved using the Pari LC Plus jet nebulizer are significantly higher than those using the Pari® LC jet nebulizer as described in Eisenberg et al. (1997), supra.

Two placebo-controlled, multicenter, randomized, double-blind clinical trials of intermittent administration of inhaled tobramycin in cystic fibrosis patients with *Pseudomonas aeruginosa* infection were reported in Ramsey, B. W. et al., "Intermittent Administration of Inhaled Tobramycin in Patients with Cystic Fibrosis. Cystic Fibrosis Inhaled Tobramycin Study Group." *N. Engl. J. Med.* 340(1):23–30 (1999). In these studies, five hundred twenty subjects were randomized to receive either 300 mg inhaled tobramycin or placebo twice daily for 28 days followed by 28 days off study drug. Subjects continued on treatment or placebo for three "on-off" cycles for a total of 24 weeks. Efficacy variables included sputum *P. aeruginosa* density. Tobramycin-treated patients had an average 0.8 $\log_{10}$ decrease in *P. aeruginosa* density from Week 0 to Week 20, compared with a 0.3 $\log_{10}$ increase in placebo-treated patients (P<0.001). Tobramycin-treated patients had an average 1.9 $\log_{10}$ decrease in *P. aeruginosa* density from Week 0 to Week 4, compared with no change in placebo-treated patients (P<0.001).

SUMMARY OF THE INVENTION

One aspect of the current invention is a method for treatment of severe chronic bronchitis or bronchiectasis caused by *Pseudomonas aureginosa* or other pseudomonads by administering to the patient requiring such treatment a formulation comprising about one to ten thousand times higher concentration of an effective aminoglycoside antibiotic, such as tobramycin, than its minimal inhibitory concentration (MIC).

In another aspect, the current invention provides methods for treatment of severe chronic bronchitis or bronchiectasis caused by *Pseudomonas aureginosa* or other pseudomonads by administering to a patient requiring such treatment effective amounts of a suitable aminoglycoside antibiotic by an endobronchial route of administration. In a representative embodiment of this aspect of the invention, the antibiotic may be endobronchially administered twice daily, for at least one day, more preferably for at least five days, and most preferably for at least fourteen days, in a formulation comprising about 8 to about 80 mg/ml of a suitable aminoglycoside antibiotic, such as tobramycin, dissolved in a full or quarter normal saline having a pH between 5.5 and 7.0. In other representative embodiments, the antibiotic may be administered in powdered form by a dry powder inhaler or metered dose inhaler, or solution form by a jet or ultrasonic nebulizer in 5 ml concentrated form in an aerosol producing a particle size having the mass medium average diameter predominately between 1 and 5μ.

Still other aspects of the current invention provide methods for treatment of severe chronic bronchitis or bronchiectasis caused by *Pseudomonas aureginosa* by administering to the patient requiring such treatment a formulation comprising about 40 to about 400 mg, more preferably about 300 mg, of a suitable aminoglycoside antibiotic, such as tobramycin, dissolved in 5 ml of a quarter normal saline adjusted to a pH about 5.5 to about 7.0.

Still another aspect of the current invention is a formulation for treatment of severe chronic bronchitis or bronchiectasis comprising a concentration from about 8 to about 80 mg/ml of tobramycin dissolved in about 5 ml of a full or quarter normal strength saline wherein said tobramycin concentration is one to ten thousand times higher than the MIC of tobramycin.

Still another aspect of the current invention is a method for treatment of severe chronic bronchitis caused by the bacteria *Streptococus pneumoniae, Haemophilus influenzae, Staphylococus aureus,* and *Moraxella catarrhalis* and the atypical pneumonias *Legionella pneumonia, Chlamydia pneumoniae,* and *Mycoplasma pneumoniae* including *Pseudomonas aeruginosa* by administering to a patient requiring such treatment a formulation of an antibiotic by aerosol delivery, wherein the formulation comprises about 8 to about 80 mg/ml of tobramycin in about 1 to about 5 ml of saline diluted into a quarter normal saline strength wherein said formulation has a pH between 5.5 and 7.0 and is delivered by a jet nebulizer in 5 ml concentrated form in an aerosol producing a particle size hating the mass medium average diameter predominantly between 1 and 5μ.

The foregoing aspects of the invention have been confirmed in a placebo-controlled, randomized study conducted to evaluate the microbiological efficacy and safety of inhaled tobramycin for treatment of patients with bronchiectasis and *P. aeruginosa*. The results obtained in bronchiectasis were highly significant, with the antimicrobial efficacy greater than 10,000 fold greater than in cystic fibrosis patients. In the study, 20% of the bronchiectasis patients had complete eradication, a finding rare with either oral or intravenous therapy. In fact, in spite of 20 years of use of intravenous tobramycin, usually in combination with another antibiotic, results such as these have not been reported. Thus, the results obtained teach the following:

1. Aerosolized aminoglycoside antibiotics can be extremely effective in treatment of bronchiectasis;
2. The aerosol route improves the efficacy of an agent even if given intravenously; and
3. The duration of therapy does not need to be long term; efficacy was seen in two weeks.

Since bronchiectasis is the most severe form of chronic bronchitis, these results teach that short course aerosol antibiotics are effective in treating the disorder.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

As used herein:

"Normal saline" means water solution containing 0.9% NaCl.

"Diluted saline" means normal saline containing 0.9% NaCl diluted into its lesser strength.

"Quarter normal saline" or "¼ NS" means normal saline diluted to its quarter strength containing 0.225% NaCl.

The current invention is based on the finding that effective aminoglycoside antibiotics, such as tobramycin, in concentrations about 8 to about 80 mg/ml are effective to substantially inhibit *Psuedomonas aeruginosa* infections when administered endobronchially in patients suffering from severe chronic bronchitis (bronchiectasis). In some patients colony forming units (CFU) of *P. aeruginosa* are decreased by a factor of about $10^6$ or more. The current invention, therefore, concerns methods for the treatment and/or prophylaxis of severe chronic bronchitis (bronchiectasis) and reduction of bacterial counts in the lung in patients in need of such treatment. In other aspects, the invention provides concentrated antibiotic formulations for the treatment of severe chronic bronchitis or bronchiectasis suitable for efficacious endobronchial delivery of an aminoglycoside antibiotic, such as tobramycin, by dry powder delivery or aerosolization into the endobronchial space.

In one aspect, the present invention provides methods for the treatment or prophylaxis of patients with chronic bronchitis comprising administering to the patient a dry powder or nebulized aerosol formulation comprising from about 1 to about 800 mg of an aminoglycoside antibiotic once or twice daily for at least one day, more preferably for at least five days and most preferably for at least fourteen days.

Aminoglycoside antibiotics useful in the practice of the invention include, for example, gentamicin, amikacin, kanamycin, streptomycin, neomycin, netilmicin and tobramycin. A presently particularly preferred aminoglycoside antibiotic for this purpose is tobramycin. Formulations according to the invention typically contain from about 20 to about 500 mg, more preferably from about 40 to about 400, and most preferably about 300 mg of aminoglycoside sulfate per 5 ml of the quarter normal saline. This corresponds to about 4 to about 100 mg/ml, more preferably about 8 to about 80 mg/ml, and most preferably about 60 m/ml of aminoglycoside, which is minimal yet efficacious amount of aminoglycoside to suppress the *Pseudomonas aeruginosa* infections in endobronchial space. Typically, about 300 mg of aminoglycoside antibiotic is dissolved in 5 ml solution of a diluted, typically quarter normal saline containing about 0.225% NaCl. Quarter normal saline, that is 0.225% of sodium chloride, is a presently preferred vehicle for delivery of aminoglycoside into endobronchial space.

Be way of illustration, high concentrations of tobramycin administered to the lungs by aerosolization result in maximization of sputum levels of tobramycin and in minimization of tobramycin serum levels. Thus, administration of tobramycin by aerosolization has the advantage of reducing systemic toxicity while providing efficacious concentrations of tobramycin in the sputum. The bronchial barrier restricts the movement of aerosolized tobramycin and prevents it from reaching high systemic levels.

Aerosolized formulation of tobramycin delivers high concentrations of the drug directly to the airways with low systemic absorption. Aerosolized formulations of concentrated tobramycin are preferably nebulized by a jet, ultrasonic or electronic nebulizer capable of producing tobramycin aerosol having a particle size predominately between 1 and 5 microns. Particles of these sizes are preferred for efficacious delivery of concentrated tobramycin into the endobronchial space in order to treat chronic bronchitis infections. To achieve high concentrations of tobramycin solution in both the upper and lower airways and in sputum, tobramycin is preferentially nebulized in jet nebulizers, particularly those modified with the addition of one-way flow valves, such as for example, Pari LC Plus™ nebulizer, commercially available from Pari Respiratory Equipment, Inc., Richmond, Va., which delivers up to 20% more drug than the other unmodified nebulizers.

The tobramycin aerosol formulation contains a high concentration from about 4 to about 100 mg/mL, more preferably about 8 to about 80 mg/ml, and most preferably about 60 mg/mL of tobramycin sufficient for *Pseudomonas aeruginosa* suppression or eradication, formulated in the smallest possible volume of about 1–5 mL of a physiologically acceptable solution, preferably in one quarter strength of normal saline, having a salinity adjusted to permit generation of tobramycin aerosol well-tolerated by patients but to prevent the development of secondary undesirable side effects such as bronchospasm and cough.

In other aspects the aminoglycoside antibiotic compounds of the invention may be endobronchially administered in a dry powder formulation for efficacious delivery of the finely milled antibiotic into the endobronchial space using dry powder or metered dose inhalers as an alternative therapy to aerosol delivery. Dry powder inhalation and metered dose inhalation are most practical when administered doses result in the delivery of at least about 10 mg, and more preferably about 15 to about 45 mg, of aminoglycoside antibiotic compound to the lung of the patient receiving treatment. Depending on the efficiency of the dry powder delivery device, which is typically about 70%, typical effective dry powder dosage levels typically fall in the range of about 20 to about 60 mg. In this aspect, the invention provides a sufficiently potent formulation of pure aminoglycoside antibiotic or a pharmaceutically acceptable salt in dry powder or metered dose form of drug particles milled to particle sizes predominantly within a range of 1 to 5 microns. Such a formulation is convenient because it does not require any further handling such as diluting the dry powder. Further it utilizes the devices that are sufficiently small, fully portable and do not require, for example, an air compressor which is needed for a jet nebulizer. Additionally, the dry powder formulation has a longer shelf-life than the liquid antibiotic formulations for aerosolization.

For dry powder formulations of the invention, a purified aminoglycoside antibiotic, or a pharmaceutically acceptable salt thereof, is milled to a powder having mass median average diameters ranging from 1–5 microns by media milling, jet milling, spray drying or particle precipitation techniques. Particle size determinations may be made using a multi-stage Anderson cascade impactor or other suitable method. Media milling may be accomplished by placing the drug substance into a mill containing, for example, stainless steel or ceramic balls and rotating or tumbling the material until the desired drug particle size ranges are achieved. Advantages of media milling include good size control, narrow product size ranges, high efficiencies of recovery, and readily scalable processes. Disadvantages include long process times (on the order of hours to days), the requirement that the milling media be separated from the product at completion, and the possibility of contamination of the product with the media. Alternatively, the dry powder formulations may be prepared by jet milling techniques. Jet milling uses very high pressure air streams to collide particles with one another, with fine particles of the desired size being recovered from the mill. Advantages include rapidity (seconds to minutes for completion) and less energy transfer during milling resulting in less temperature rise of drug product. Disadvantages include poorer collection efficiencies (50 to 80% recovery is typical). Both techniques and any and all improvements thereof are intended to be within the scope of the invention.

In other embodiments, the dry powder formulations may be prepared by spray drying or solution precipitation techniques. Spray drying is achieved by spraying a fine mist of drug solution onto a support and drying the particles. The particles are then collected. Spray drying has the advantage of being the least prone to degrading chemical entities. Solution precipitation is performed by adding a co-solvent that decreases the solubility of a drug to a uniform drug solution. When sufficient co-solvent is added the solubility of the drug falls to the point where solid drug particles are formed which can be collected by filtration or centrifugation. Precipitation has the advantage of being highly reproducible and can be performed under low temperature conditions which reduce degradation.

The dry powder formulations of the invention may be used directly in metered dose or dry powder inhalers. A metered dose inhaler consists of three components: a canister containing the propellant/drug suspension, a metering value designed to deliver accurately metered volumes of the propellant suspension, and an oral adapter which contains a spray orifice from which the metered dose is delivered. In the rest position, the metering chamber of the value is connected to the drug suspension reservoir via a filling groove or orifice. On depression of the value this filling groove is sealed and the metering chamber is exposed to atmospheric pressure via the spray orifice in the oral adapter and the valve stem orifice. This rapid pressure reduction leads to flash boiling of the propellant and expulsion of the rapidly expanding mixture from the metering chamber. The liquid/vapor mixture then enters the expansion chamber, which is constituted by the internal volume of the value stem and the oral adapter. The mixture undergoes further expansion before being expelled, under its own pressure, from the spray nozzle. On exit from the spray orifice, the liquid ligaments which are imbedded in propellant vapor are torn apart by aerodynamic forces. Typically, at this stage the droplets are 20 to 30 microns in diameter and are moving at the velocity of sound of the two-phase vapor liquid mixture (approximately 30 meters/second). As the cloud of droplets moves away from the spray nozzle, it entrains air from the surroundings and decelerates, while the propellant evaporates through evaporation, the entrained droplets eventually reach their residual diameter. At this point, the particles/droplets consist of a powdered drug core coated with surfactant. Depending on the concentration and the size of the suspended material the powdered drug core can consist of either individual drug particles or aggregates. Currently, metered dose inhaler technology is optimized to deliver masses of 80 to 100 micrograms of drug, with an upper limitation of 1 mg of drug deliverable.

An alternate route of dry powder delivery is by dry powder inhalers. There are two major designs of dry powder inhalers, device-metering designs in which a reservoir of drug is stored within the device and the patient "loads" a dose of the device into the inhalation chamber, and factory-metered devices in which each individual dose has been manufactured in a separate container. Both systems depend upon the formulation of drug into small particles of mass median diameters form 1 to 5 microns, and usually involve coformualtion with larger excipient particles (typically 100 micron diameter lactose particles). Drug powder is placed into the inhalation chamber (either by device metering or by breakage of a factory-metered dosage) and the inspiratory flow of the patient accelerates the powder out of the device and into the oral cavity. Non-laminar flow characteristics of the powder path cause the excipient-drug aggregates to decompose, and the mass of the large excipient particles causes their impaction at the back of the throat, while the smaller drug particles are deposited deep in the lungs. Current technology for dry powder inhalers is such that payload limits are around 10 mg of powder (of which drug is usually a minor component by mass).

Effective dosage levels of aminoglycoside antibiotic for dry powder inhalation and metered dose inhalation result in the delivery of at least about 10 mg, and more preferably about 15 to about 45 mg, of aminoglycoside antibiotic compound to the lung of the patient receiving treatment. Depending on the efficiency of the dry powder delivery device, dry powder formulations suitable for use in the invention comprise from about 0.5 to about 100 mg, preferably from about 20 to about 60 mg, of powder in an amorphous or crystalline state in particle sizes between 1 and 5 microns in mass median average diameter necessary for efficacious delivery of the antibiotic into the endobronchial space for treatment and prevention of *Pseudomonas aeruginosa*. The dry powder formulation may be delivered from 1 to 4 times daily, preferably twice daily, for a period of at least one day, more preferably at least 5 days and most preferably at least fourteen days. The dry powder formulations are temperature stable and have a physiologically acceptable pH of 4.0–7.5, preferably 6.5 to 7.0, and long shelf lives.

The tobramycin aerosol formulation of the invention contains at least one thousand but usually about ten thousand times higher concentration of tobramycin than is its minimum inhibitory amount. Tobramycin is nebulized predominantly into particle sizes which are delivered to the terminal and respiratory bronchioles and alveoli (lower lungs) where the respiratory pathogens are present. Moreover, high concentration of aerosolized tobramycin comes into contact with the sputum, penetrates it and kills bacteria present there.

Figure 1:
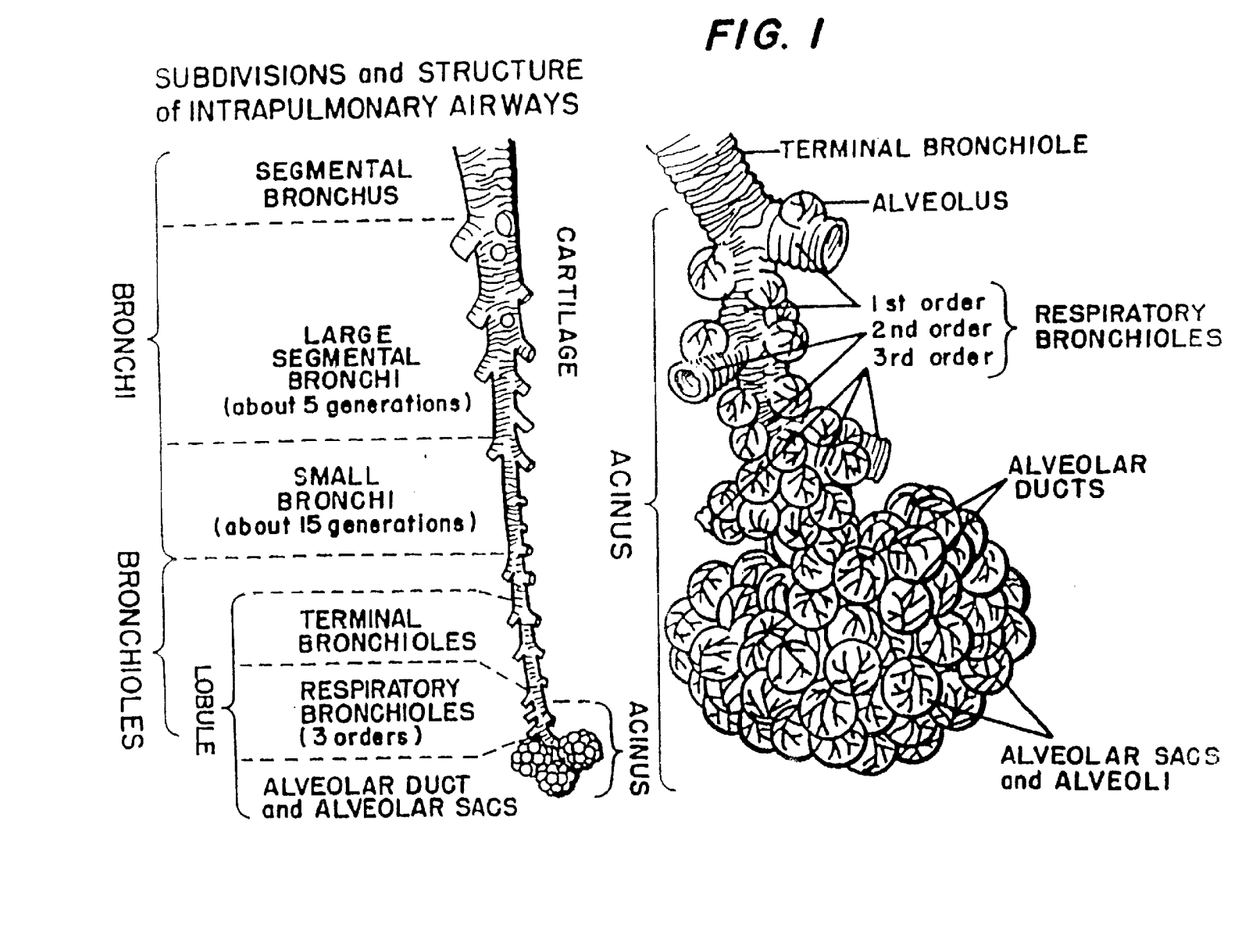
FIG. 1 depicts subdivisions and structure of intrapulmonary airways.

Subdivision and structure of intrapulmonary airways (lower lung) are seen in FIG. 1. Respiratory microbial pathogens are present in the upper airways, in bronchi and bronchioli, particularly in terminal and respiratory bronchioles. During exacerbation of infection, bacteria can also be found to be present in alveoli. Any therapeutic formulation must be, therefore, delivered to the terminal bronchioles and to alveoli.

The foregoing and other aspects of the invention may be better understood in connection with the following representative examples.

EXAMPLE 1

In Vivo Clinical Study

A placebo-controlled, double-blind, randomized study was conducted to evaluate the microbiological efficacy and safety of inhaled tobramycin for treatment of patients with bronchiectasis and *P. aeruginosa*. Patients with *P. aeruginosa* ($\geq 10^4$ colony forming units/g sputum) were randomly assigned to receive either Tobramycin Solution for Inhalation (TSI) (n=37) or placebo (n=37) twice daily for 4 weeks. The change in *P. aeruginosa* density in sputum was measured at Weeks 2, 4, and 6 (2 weeks post-treatment). Clinicians assessed patients' general medical condition at Week 6. Safety parameters included adverse events, serum chemistry, and airway reactivity. At Week 4, the TSI group had a mean decrease in *P. aeruginosa* of 4.54 $\log_{10}$ colony forming units/g sputum compared with no change in the placebo group (p<0.001). At Week 6, *P. aeruginosa* was eradicated in 35% of TSI-treated patients but was detected in all placebo patients. Investigators indicated 62% of TSI patients versus 38% of placebo patients showed an improved medical condition (odds ratio=2.7, 95% CI: 1.1–6.9). More TSI-treated patients than placebo patients reported increased cough, dyspnea, wheezing, and non-cardiac chest pain, but the symptoms did not limit therapy. Few patients withdrew due to adverse events. TSI holds promise as a therapy for patients with bronchiectasis. The study was conducted as follows:

Patients were recruited from 16 sites across the United States. The institutional review board at each site approved the study protocol and informed consent. After discussing the study with the site investigator, all patients signed informed consent forms and then proceeded with screening.
Study Design Patients included in this study had a diagnosis of bronchiectasis confirmed by conventional or high resolution computed tomography and had grossly purulent sputum containing, at minimum, $10^4$ colony forming units (CFU) *P. aeruginosa* per gram. Patients were excluded if they had CF, a diagnosis of allergic bronchopulmonary aspergillosis, an acute pulmonary process requiring medical intervention as indicated by a new infiltrate on a chest radiograph, significant recent hemoptysis, or had received antibiotics within two weeks of the screening visit.

Eligible patients were randomly assigned in blocks of two to parallel groups at each study center to receive either TSI or placebo. TSI (TOBI®, PathoGenesis Corporation, Seattle, Wash.) is a non-pyrogenic, preservative-free, pH-adjusted solution designed for inhalation. Each 5 mL dose of TSI contains 300 mg tobramycin and 11.25 mg sodium chloride in sterile water for injection. The placebo, 1.25 mg quinine sulfate in the same excipient, was chosen because its taste is similar to tobramycin. Patients in both treatment groups self-administered the study drug twice daily for 28 days using a PARI LC PLUS™ jet nebulizer (Pari, Richmond, Va.) and a Pulmo-Aide® compressor (DeVilbiss, Somerset, Pa.).

Study visits were scheduled every 2 weeks during the 8-week study. The first dose of drug was administered at Week 0, two weeks after screening. Patients visited the clinic for an interim visit at Week 2, for the last day of treatment at Week 4, and for a follow-up visit at Week 6. Patients were withdrawn from the study if they required additional antibiotic treatment at any time during study participation.

At all study visits, vital signs were measured, adverse events were recorded, and a sputum sample was collected for quantitative microbiology and susceptibility testing. At Week 0, prior to and 30 minutes after the patient administered study drug, the forced expiratory volume at one second ($FEV_1$) was measured by standard American Thoracic Society methodology to monitor airway reactivity (American Thoracic Society. Standardization of spirometry, Amer J Respir Crit Care Med 1995; 152:1107–36). Blood was drawn 30–60 minutes after drug administration for analysis of serum tobramycin concentration. At Week 4, airway reactivity was again monitored, a medical exam was performed, and laboratory tests that were performed at screening were repeated.

Serum chemistry, hematology, and serum tobramycin concentrations were performed at a central laboratory. Quantitative sputum bacterial culture and measurement of tobramycin minimum inhibitory concentrations (MIC) for *P. aeruginosa* were performed at a central laboratory (Children's Hospital and Regional Medical Center, Seattle, Wash.) as described by Burns et al., "Microbiology of sputum from patients at cystic fibrosis centers in the United States," *Clin Infect Dis* 27:158–63 (1998). Sputum samples collected at each study visit were shipped on wet ice for receipt within 48 hours at the central laboratory.
Endpoints The primary efficacy endpoint was the change in *P. aeruginosa* density (expressed as $\log_{10}$ CFU/g sputum) from baseline to Week 4. Additional efficacy endpoints included the following: (1) the change in *P. aeruginosa* density from baseline to Week 2 and to Week 6; (2) an investigator's assessment of change in the patient's general medical condition ("improved" or "not improved") throughout the study (recorded at Week 6); (3) the percent change in $FEV_1\%$ predicted and in forced vital capacity (FVC) % predicted from Week 0 to Week 4. Percent predicted values were calculated by dividing the actual values of $FEV_1$ or FVC by the values predicted by the Knudson equations for normal, healthy individuals based on gender, age, and height and multiplying by 100.[20] Safety endpoints included the incidence of adverse events, change in serum chemistry and hematology measurements, and airway reactivity.

Each patient's microbiological response was categorized according to whether *P. aeruginosa* was eradicated, reduced by treatment, or did not respond to treatment. *P. aeruginosa* was considered eradicated if it was not detected at Week 6 or if the patient was unable to produce a sputum sample at Week 6 and *P. aeruginosa* was not isolated at Week 4. A patient's response was defined as reduced by treatment if *P.* aeruginosa was recovered from the Week 6 sputum sample but was reduced by at least 2 $\log_{10}$ CFU/g at Week 4. A patient had no microbiological response if *P. aeruginosa* did not decrease 2 $\log_{10}$ CFU/g at Week 4 or if the patient withdrew from the study.

Statistical Analysis

The sample size calculation was based on 85% power to detect a 1.0 $\log_{10}$ difference in *P. aeruginosa* density between the treatment groups. All patients who received at least one dose of either TSI or placebo (intent-to-treat) were included in the statistical analyses. The groups were compared with respect to the mean change from baseline in *P. aeruginosa* density using two-sample, two-sided t-tests. The measurement at Week 0 was used as the baseline value unless unavailable; in that event, the measurement at the screening visit was used. Any result of "no *P. aeruginosa* isolated" was numerically represented as 19 CFU/g, 1 CFU/g below the limit of detection for the quantitative bacterial culture.

The relationship between baseline characteristics and investigator's assessment of patients' general medical condition (improved, not improved) at Week 6 was analyzed using logistic regression. Logistic regression was also used to assess the relationship between general medical condition and change in *P. aeruginosa* density.

An adverse event was defined as treatment-emergent if (1) it was not present at baseline and occurred after the start of study medication; or (2) it was present at baseline but increased in severity after the start of study medication; or (3) it was considered by the investigator to be related to study medication. Within each treatment group, airway reactivity (percent change in $FEV_1$ from pre- to post-study drug administration) was analyzed using the Wilcoxon signed rank test.

Results

Figure 2:
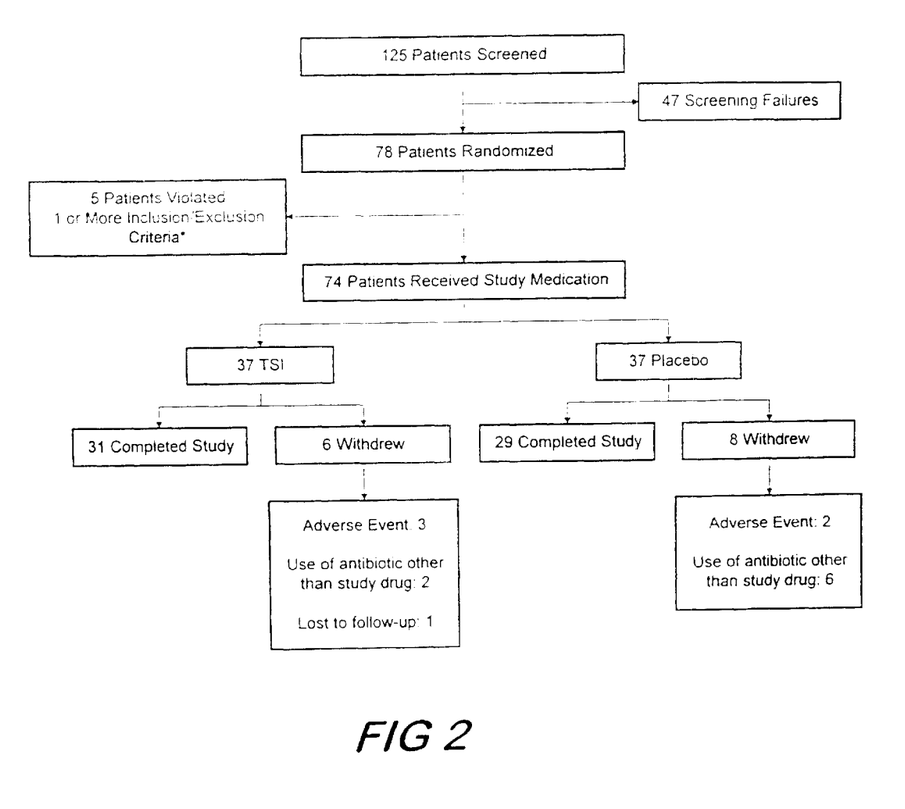
FIG. 2 is an outline of the study described in Example 1.

One hundred twenty-five patients were screened for this study (see FIG. 2). A majority of the 47 patients who failed screening did so because their sputum contained less than $10^4$ CFU/g *P. aeruginosa*. Seventy-eight patients were randomized and 74 patients received at least one dose of study drug; 37 received TSI and 37 received placebo. Similar numbers of patients in each treatment group withdrew from the study, 6 of 37 (16%) in the TSI group and 8 of 37 (22%) in the placebo group. As shown in the following Table 1, the treatment (groups were similar at baseline with respect to gender, age, race, *P. aeruginosa* density in sputum, and pulmonary function. Both treatment groups adhered to the dosing requirements; 81% of patients in the TSI group and 86% in the placebo group used more than 80% of the drug doses.

TABLE 1

Demographics and Baseline Characteristics

| Characteristic | TSI (n = 37) | Placebo (n = 37) | p-value |
|---|---|---|---|
| Gender | | | |
| Female* | 23 (62.2%) | 22 (59.5%) | 1.000‡ |
| Age in years† | 66.6 (13.0) | 63.2 (13.5) | 0.270§ |
| Race | | | |
| Caucasian* | 36 (97.3%) | 32 (86.5%) | 0.199‡ |
| *P. aeruginosa* $\log_{10}$ CFU/g sputum† | 7.1 (1.4) | 6.7 (1.6) | 0.331§ |
| $FEV_1$ % predicted† | 56.2 (21.2) | 53.3 (22.1) | 0.574§ |

TABLE 1-continued

Demographics and Baseline Characteristics

| Characteristic | TSI (n = 37) | Placebo (n = 37) | p-value |
|---|---|---|---|
| Duration of bronchiectasis in years† | 14.1 (15.4) | 18.7 (17.0) | 0.232§ |
| History of smoking* | 24 (64.9%) | 16 (43.2%) | 0.102‡ |

*n (%)
†Mean (SD)
‡Treatment groups were compared using Fisher's Exact test.
§Treatment groups were compared using two-sample, two-sided tests.

Figure 3:
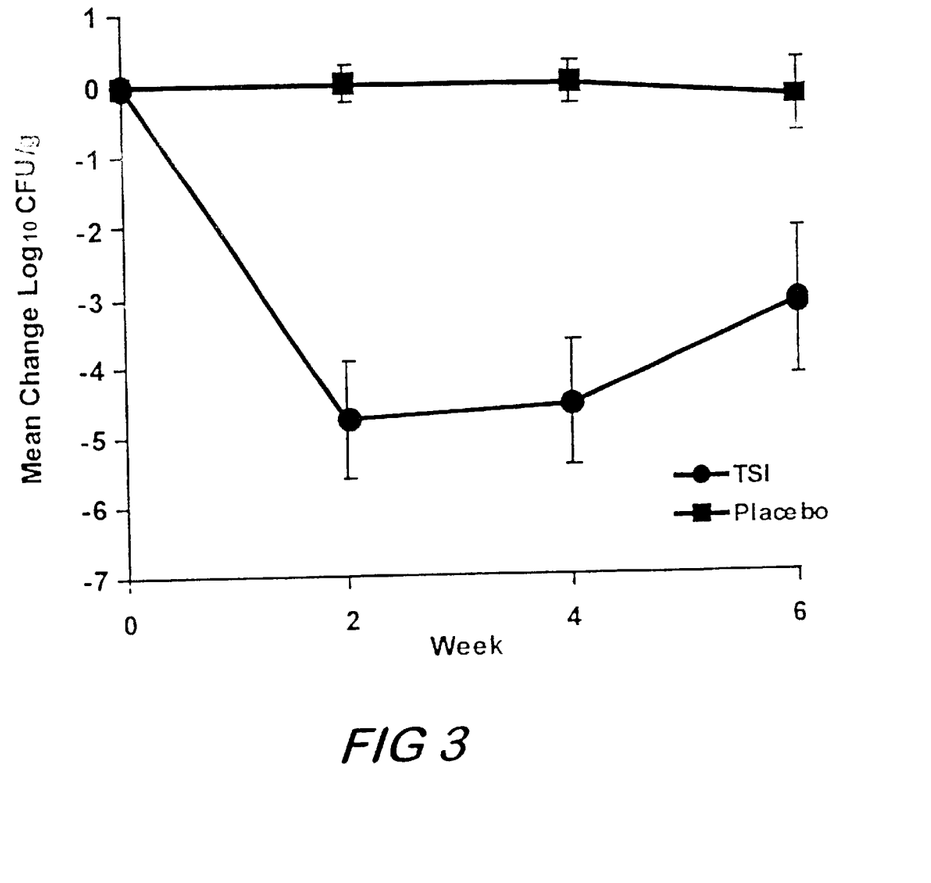
FIG. 3 is a graphical representation of the mean change in sputum *P. aeruginosa* density, as described in Example 1. Patients received TSI or placebo twice daily between Weeks 0 and 4. At baseline, n=37 for both groups. The error bars shown in FIG. 3 represent 95% confidence intervals.

As shown in FIG. 3, at all time points of the study, patients treated with TSI had a significant reduction in sputum *P. aeruginosa* compared with patients treated with placebo. At the end of treatment (Week 4), TSI-treated patients had a mean decrease of 4.54 $\log_{10}$ CFU/g sputum compared with a mean increase of 0.02 $\log_{10}$ CFU/g sputum in patients receiving placebo (p<0.001). After the two-week follow-up period (Week 6), the mean reduction observed in the TSI group was smaller than at previous weeks, indicating that some re-growth of the organism had occurred following the cessation of TSI therapy. The placebo group showed negligible change in *P. aeruginosa* density at all time points.

At the end of the study (Week 6), more TSI-treated patients (23 of 37, 62%) than placebo-treated patients (14 of 37, 38%) were assessed as having an improved medical condition. The odds that a patient receiving TSI would improve were 2.7 times higher than for a patient who received placebo (95% CI: 1.1–6.9). In addition to treatment group, gender was also a significant predictor of clinical improvement; 62% of women were assessed as improved compared with 31% of men (p=0.010). Other baseline characteristics, e.g., whether the patient smoked and baseline $FEV_1$, were not predictive. Logistic regression analyses performed to evaluate the relationship between clinical improvement and change in *P. aeruginosa* density showed that decreases in CFU/g sputum at Weeks 2 (p=0.005), 4 (p=0.003), and 6 (p=0.039) were significant predictors of improved medical condition.

Examination of individual patient's microbiological response showed that one-third (13 of 37) of the TSI-treated patients had *P. aeruginosa* eradicated from their sputum. An additional third (12 of 37) showed a reduction of at least 2 $\log_{10}$ in *P. aeruginosa* density at Week 4. The last third (12 of 37) of TSI-treated patients had no microbiological response. In contrast, 33 of 35 (94%) of the placebo patients had no microbiological response and only 2 of 35 (6%) had greater than a 2 $\log_{10}$ decrease in *P. aeruginosa* density. Two of the 37 placebo patients were not evaluable for microbiological response.

Increased resistance of bacteria to a drug is a common consequence of treating chronically infected patients with antibiotics. Because a resistance breakpoint for administration of aerosolized tobramycin to treat *P. aeruginosa* has not been established, the value for parenteral administration (MIC >16 $\mu$g/mL)[21] was used to determine the number of patients who had resistant *P. aeruginosa* develop during the course of treatment. Four of 36 (11%) patients in the TSI group and 1 of 32 (3%) patients in the placebo group who began the study with susceptible *P. aeruginosa* had resistant *P. aeruginosa* at their last visit (p=0.360).

Changes in pulmonary function were not significantly different between the treatment groups. The mean percent change from Week 0 to Week 4 in $FEV_1$% predicted was similar for the TSI and placebo groups (−2.2% vs. 1.5%, respectively, p=0.408). The mean percent change in FVC % predicted was also similar for both TSI and placebo groups (−2.8% vs. 2.2%, respectively, p=0.187).

Thirty-one of 37 (84%) patients in each treatment group reported at least one treatment-emergent adverse event. Respiratory system adverse events were reported by 26 (70%) TSI patients and by 19 (51%) placebo patients. Symptoms that were reported by more TSI-treated patients included increased cough, dyspnea, wheezing, and chest pain (Table 2).

TABLE 2

Incidence of Treatment-Emergent Adverse Events Occurring in Greater than 10% of TSI Patients

| Symptom | TSI (n = 37) | Placebo (n = 37) |
|---|---|---|
| Patients reporting 1 adverse event* | 31 (83.8%) | 31 (83.8%) |
| Increased cough | 15 (40.5%) | 9 (24.3%) |
| Dyspnea | 12 (32.4%) | 3 (8.1%) |
| Increased sputum | 8 (21.6%) | 5 (13.5%) |
| Chest pain | 7 (18.9%) | 0 |
| Wheezing | 6 (16.2%) | 0 |
| Fatigue | 5 (13.5%) | 6 (16.2%) |
| Hemoptysis[†] | 5 (13.5%) | 3 (8.1%) |
| Fever | 4 (10.8%) | 6 (16.2%) |
| Decreased sputum production | 5 (13.5%) | 0 |

*n (%)
[†]Mild or moderate, including blood-streaked sputum: no severe hemoptysis occurred in either group.

Events reported as chest pain appeared to be related to the respiratory system based on investigator comments (e.g., chest tightness and pleuritic pain) and on the treatment interventions (bronchodilators and analgesics). Physicians commented that the adverse events were related to study drug for 12 of 15 TSI-treated patients reporting increased cough, for 3 of 12 patients experiencing dyspnea, for 3 of the 6 patients with wheezing, and for 3 of the 7 patients reporting chest pain.

Patients hospitalized and treated for exacerbation of their pulmonary disease included 4 patients in the TSI group and one patient in the placebo group. The placebo patient and 3 of the 4 TSI-treated patients were treated with intravenous antibiotics. The fourth TSI patient received anti-inflammatory drugs but continued to administer TSI while in the hospital. The patient completed the study and *P. aeruginosa* was eradicated from her sputum. Another TSI-treated patient who withdrew from the study experienced an increase in respiratory symptoms and was hospitalized for treatment several days after withdrawal.

Acute airway reactivity, defined for this study as a decrease of greater than 12% in $FEV_1$ 30 minutes after drug administration, occurred in 3 of 36 (8.3%) TSI patients and in 6 of 37 (16.2%) placebo patients. All of the TSI-treated patients and 4 of 6 placebo patients were prescribed bronchodilators prior to entering the study, indicating each had a history of reactive airways.

Overall, no clinically significant changes in laboratory values, including BUN and creatinine, occurred in patients in either treatment group. The median tobramycin concentration in serum of TSI-treated patients measured 30–60 minutes after drug administration was 0.54 μg/mL and ranged from the lower limit of detection (0.18 μg/mL) to 2.64 μg/mL.

EXAMPLE 2

Nebulizer Evaluation

For the practice of the present invention with aerosol formulations, it is important to use a jet or ultrasonic nebulizer able to nebulize the formulation of the invention into aerosol particle size predominantly in the range from 1–5μ. Predominantly in this application means that at least 70% but preferably more than 90% of all generated aerosol particles are within 1–5μ range.

Two types of nebulizers such as jet and ultrasonic, can produce and deliver particles between the 1 and 5μ particle size that is optimal for treatment of *Pseudomonas aeruginosa* infections are currently available. A jet nebulizer works by air pressure to break a liquid solution into aerosol droplets. An ultrasonic nebulizer works by a piezoelectric crystal that shears a liquid into small aerosol droplets. However, only some formulations of tobramycin can be efficiently nebulized by both nebulizers as both devices are sensitive to the pH of the formulation and to its ionic strength. The formulations which can be nebulized typically must contain large amounts of erythromycylamine which is delivered in large volumes of aerosol.

While the range variety of nebulizers is available, only limited number of these nebulizers are suitable for the purposes of this invention. The suitable nebulizer for the purposes of this invention is illustrated in FIG. 4.

Figure 4:
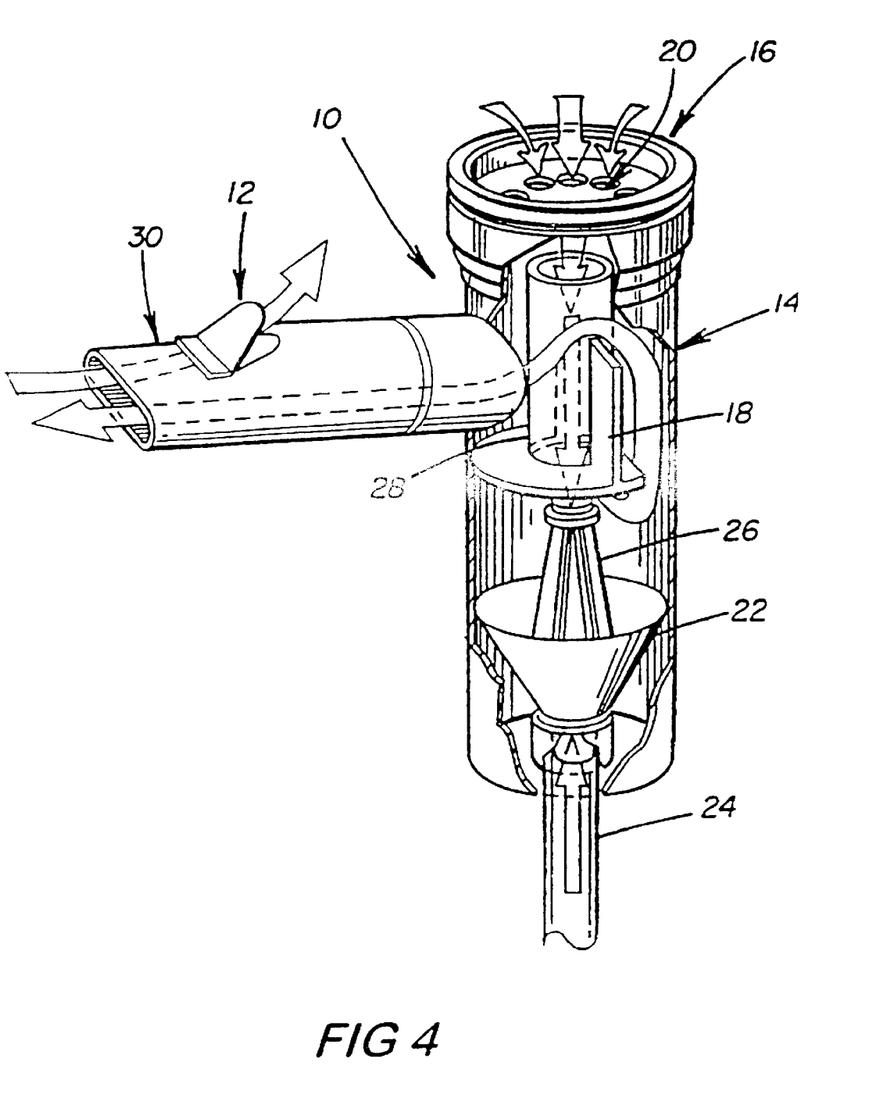
FIG. 4 depicts a jet nebulizer suitable for aerosolization of an concentrated antibiotic solution of the invention.

FIG. 4 shows the jet nebulizer 10 useful for aerosolization of tobramycin.

The liquid formulation is placed into the nebulizer cup 22 by removing and replacing the cup's cap 16. The cap 16 has one or more air intake holes 20 that allow entrainment of room air to Venturi chamber 28. Venturi chamber 28 allows entrained room air to mix with aerosol to increase drug delivery. Air supply tube 24, typically (8 l/M) is connected to nebulizer's liquid medicine cup 22. Air goes through the cup 22 into jet nebulizer orifice 26 where it creates aerosol by shearing the liquid solution into small threads of liquid that shatter into small particles when it hits a baffle 18. The nebulizer 10 further comprises a mouthpiece 30 for inhalation of aerosol. The mouthpiece contains flapper valve 12 to allow exhalation. The mouthpiece 30 is connected to the main body of the nebulizer 10.

To identify efficient and suitable nebulizer for use in the current invention, two separate studies were performed.

The first study, described below, was to determine in vitro which nebulizers meet criteria that are important for delivery of aerosolized antibiotics. Both ultrasonic and jet nebulizers were studied. The second study was to determine the pharmacodynamics of tobramycin in the sputum which is a measure of the efficacy of the aerosol delivery.

The major limitation of the Ultraneb® 99 (DeVilbiss) ultrasonic nebulizer used for delivery of tobramycin formulation are its high-cost, waste of the drug and inconvenience. As seen from Table 3, this nebulizer requires 30 ml of the drug solution, and it has large, 1200 ml aerosol reservoir. In order for tobramycin aerosol therapy to be widely available and used by patients with chronic bronchitis in ambulatory or home setting, a more efficient and easier to use nebulizer is needed.

This study was the first step in testing whether the first jet nebulizer could be substituted for ultrasonic nebulizer and whether adequate sputum aminoglycoside levels can be obtained with a jet nebulizer. Subsequent studies included long-term clinical efficacy.

An in vitro comparative stud) evaluated a variety of commercially available jet nebulizers, including among others, the Acorn II® by Marquest, T-Updraft® by Hudson, Sidestream® by Medicaid, and Pari LC® by Pari. The PulmoAide® compressor was designed.

A closer look at all these nebulizers revealed that most of them are relatively inefficient in delivering an inhalable mist.

The three chosen nebulizers used in the clinical protocols, the ultrasonic DeVilbiss 99, the Pari LC jet and the Medicaid Sidestream jet, have shown properties suggesting that they could possibly deliver tobramycin aerosol into endobronchial space. Of the three, two jet nebulizers were clearly superior to the ultrasonic DeVilbiss. Therefore, they have been evaluated in vitro to determine which one of them could provide the greatest amount of drug to the airways and two jet nebulizers were found to meet the requirements.

A comparative characteristics of the Ultraneb® 99 DeVilbiss (ultrasonic) and two of the jet nebulizers, the Sidestream® and the Pari® LC with the PulmoAide® compressor, showing the best in vitro characteristics, are listed in Table 1.

TABLE 3

Comparative Characteristics of Different Nebulizers

| Nebulizer | DeVilbiss | Sidestream | Pari LC |
|---|---|---|---|
| Type | Ultrasonic | Jet | Jet |
| Airflow | 8 L/m | 8 L/m | 8 L/m |
| Liquid Reservoir | 30 ml | 5 ml | 5 ml |
| Time to Nebulize | 10–12 min | 13 min | 10 min |
| Erythromycylamine Formulation | 20 mg/ml in ½ NS | 60 mg/ml in ¼ NS | 60 mg/ml in ¼ NS |
| MMAD | 4–5 microns | 2.2 microns | 4–5 microns |
| Drug Dose/ml | 33 ± 1.8 mg | 30 ± 1.8 mg | 30 ± 5 mg |
| Total Drug Dose | 600 mg | 300 mg | 300 mg |

As seen from Table 3, there are substantial differences between the ultrasonic and jet nebulizer systems. The two jet nebulizers require about six times smaller solution volume and do not have or require a large reservoir from which the aerosol can be inhaled. In terms of the dosage, for example, 600 mg dosage was used in the DeVilbiss 99 ultrasonic nebulizer while only one-half of that amount was found to be sufficient for use in jet nebulizer. To achieve the 600 mg dosage in jet nebulizer, the formulation required in a jet nebulizer would be 120 mg/ml in a 5 ml solution that is twice as large as is needed. Under these conditions, the solute tonicity would need to be decreased to maintain physiologic osmolarity of the solution. The osmolarity is the sum of the osmoles of erythromycylamine and the saline in the solution. Physiologic osmolarity is a range that does not induce bronchospasm or cough.

Of the two jet nebulizers compared in Table 3, the Sidestream may be more efficient in delivery aminoglycoside to the lower airway because of the smaller (2.2$\mu$) particle size output. Conversely, the Pari LC produces a larger particle size (4.5$\mu$) at a higher output thus reducing the delivery time and patient's discomfort. Both jet nebulizers have a Venturi design which increases dug delivery within inspiration. The smaller equipment size decreases the fallout of aerosolized particles that occurs prior to inspiration by the patient. The jet nebulizers Sidestream and Pari LC also have the advantage of being available in both reusable disposable units.

As also seen in Table 3, all three nebulizers delivered about 30 mg/ml of tobramycin to the airways even though the ultrasonic DeVilbiss 99 nebulizer needed twice as much drug, that is 600 mg of tobramycin compared with 300 mg for the two jet nebulizers, for delivery of 33 mg/ml.

The current invention tested and identified two jet nebulizers which are able to deliver the tobramycin efficacy equivalence by using only one-half of the dosage needed by ultrasonic nebulizer.

In addition to the above tested jet nebulizers, two small volume ultrasonic nebulizers. Aerosonic by DeVilbiss and UltraAire by Omron were also tested and found suitable for delivery of the formulation of the invention. These ultrasonic nebulizers differ from the UltraNebb 99 ultrasonic as they have a smaller reservoir and can use the smaller volume solution.

UTILITY

The utility of this invention is that this small volume, high concentration formulation of an aminoglycoside, such as tobramycin, can be used by either a jet or hand-held ultrasonic nebulizer and deliver efficacious concentrations of the drug to the endobronchial space in people with severe chronic bronchitis (bronchiectasis) due to aminoglycoside susceptible bacteria or other infections. The formulation is safe and very cost effective. Furthermore, the formulation is kept in a nitrogen environment and with pH controlled to provide adequate shelf life for commercial distribution.

While the preferred embodiments of the invention have been illustrated and described, it will be appreciated that various changes can be made therein without departing from the spirit and scope of the invention.

The embodiments of the invention in which an exclusive property or privilege is claimed are defined as follows:

1. A method for the treatment of patients with chronic bronchitis comprising administering to the patient a dry powder or nebulized aerosol formulation comprising from about 1 to about 500 mg of an aminoglycoside antibiotic once or twice daily for at least five days.

2. The method of claim 1 wherein the amino glycoside antibiotic is selected from the group consisting of gentamycin, amikacin, kanamycin, streptomycin, neomycin, netilmicin and tobramycin.

3. The method in claim 2 wherein the amino glycoside antibiotic is gentamycin.

4. The method in claim 2 wherein the amino glycoside antibiotic is amikacin.

5. The method in claim 2 wherein the amino glycoside antibiotic is kanamycin.

6. The method in claim 2 wherein the amino glycoside antibiotic is streptomycin.

7. The method in claim 2 wherein the amino glycoside antibiotic is neomycin.

8. The method in claim 2 wherein the amino glycoside antibiotic is netilmicin.

9. The method in claim 2 wherein the amino glycoside antibiotic is tobramycin.

10. The method in claim 1 wherein the antibiotic is administered in an aerosol or in a dry powder form.

11. The method in claim 10 wherein the antibiotic is administered in an aerosol form.

12. The method of claim 11 wherein the aerosol is delivered by a jet ultrasonic or electronic nebulizer.

13. The method in claim 11 wherein the antibiotic is administered in a formulation that upon aerosolization has particle sizes between about 1 and 5 microns.

14. The method in claim 10 wherein the antibiotic is administered in a dry powder form.

15. The method of claim 14 wherein the dry powder is delivered by a dry powder inhaler or by a metered dose inhaler.

16. The method in claim 12 wherein the dry powder has particle sizes between about 1 and 5 microns.

17. The method in claim 10 wherein the antibiotic is administered in a formulation have a pH between about 5.5 and 6.5.

18. A method of claim 1 wherein from about 1 to 400 mg of the antibiotic is administered twice daily for at least five days.

19. A method of claim 18 wherein from about 100 to 400 mg of tobramycin is administered twice daily for at least five days.

20. A method in claim 19 wherein from about 250 to about 350 mg of tobramycin is administered twice daily for at least five days.

21. A method in claim 19 wherein about 300 mg of tobramycin is administered twice daily for at least five days.

22. A method for the treatment of bronchitis comprising administering to patient in need of such treatment an endobronchial formulation comprising about 250 to about 350 mg of tobramycin dissolved in about 5 ml of solution containing a quarter normal saline adjusted to pH between about 5.5 and 6.5 and administered by nebulization using an ultrasonic nebulizer able to produce predominantly aerosol particle sizes between 1 and 5 microns.

* * * * *